(12) United States Patent
Reeves et al.

(10) Patent No.: US 6,303,810 B1
(45) Date of Patent: Oct. 16, 2001

(54) PROCESS FOR MANUFACTURING BIS-SILYL UREAS

(75) Inventors: David Reeves, Francheville; Christophe Ruppin, Pierre-Benite; Gilles Drivon, Saint Martin en Haut, all of (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/589,121

(22) Filed: Jun. 8, 2000

(30) Foreign Application Priority Data

Jun. 8, 1999 (FR) .................................................. 99 07206

(51) Int. Cl.$^7$ ....................................................... C07F 7/10
(52) U.S. Cl. ................ 556/421; 252/182.3; 252/182.34; 252/183.11
(58) Field of Search .................... 556/421; 252/182.3, 252/182.34, 183.11

(56) References Cited

U.S. PATENT DOCUMENTS

| 2,966,507 | * | 12/1960 | Montgomery | 556/421 |
| 3,049,559 | * | 8/1962 | Montgomery | 556/421 |
| 3,208,971 | * | 9/1965 | Gilkey et al. | 556/421 |
| 3,895,043 | * | 7/1975 | Wagner et al. | 556/421 |
| 3,992,428 | | 11/1976 | Müller et al. | 260/448.2 E |
| 4,379,923 | | 4/1983 | Bruynes et al. | 544/26 |
| 4,400,509 | | 8/1983 | Bruynes et al. | 544/315 |
| 4,600,790 | * | 7/1986 | Eck et al. | 556/421 |

FOREIGN PATENT DOCUMENTS 0 043 630    1/1982  (EP) .

* cited by examiner

Primary Examiner—Paul F. Shaver
(74) Attorney, Agent, or Firm—Millen, White, Zelano & Branigan, P.C.

(57) ABSTRACT

The invention relates to a process for manufacturing bis-silyl ureas which consists in reacting urea and a disilazane in an aliphatic nitrile and most particularly in acetonitrile. The process of the present invention applies particularly to the manufacture of bis(trimethylsilyl)urea from urea and hexamethyldisilazane.

22 Claims, 1 Drawing Sheet

PROCESS FOR MANUFACTURING BIS-SILYL UREAS

FIELD OF THE INVENTION

The present invention relates to a process for manufacturing bis-silyl ureas.

BACKGROUND OF THE INVENTION

Bis-silyl ureas are used as intermediates in the synthesis of pharmaceutical products. Thus, 1,3-bis(trimethylsilyl)urea (BSU) is used in the synthesis of antibiotics such as ampicillin and cephalexin.

The main routes of access to the bis-silyl ureas (I) comprise processes which consist in reacting a disilazane (II) and urea according to equation (1):

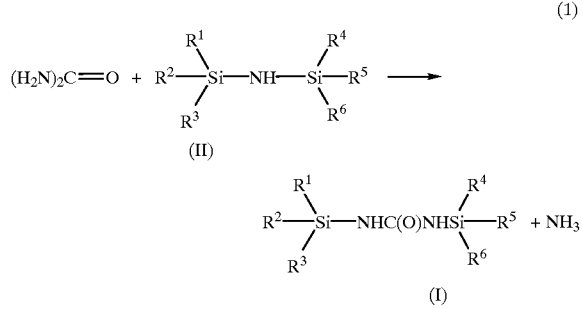

$R^1$, $R^2$, $R^3$, $R^4$, $R^5$ and $R^6$ in formulae I and II, which may be identical or different, represent a linear or branched aliphatic hydrocarbon-based radical containing from 1 to 5, a phenyl radical, a benzyl radical or a phenethyl radical.

The processes using this synthetic route are very similar and differ only in the use of different catalysts, variable urea/(II) molar ratios, different solvents and in the use of more or less pure reagents, in particular in the use of a urea which has very different particle sizes.

It is necessary to use a catalyst; otherwise reaction (1) is slow or does not take place. The reaction temperature can be increased in order to accelerate the reaction, but this increase in temperature is liable to bring about the more or less substantial degradation of the products obtained, with formation of impurities that are difficult to remove. Thus, all the processes of which we are aware use catalysts.

Most of the catalysts used are ammonium salts such as ammonium chloride or ammonium sulphate, mentioned in U.S. Pat. No. 3 992 428, Lewis acids such as $BCl_3$, $TiCl_4$ or $AlCl_3$, or inorganic acids such as HBr or $H_3PO_4$, also mentioned in U.S. Pat. No. 3 992 428, chlorosilanes such as trimethylchlorosilane mentioned in Patent Application FR 2 333 805, nitrogenous compounds containing electron-withdrawing groups, such as saccharin mentioned in Patent Application EP 43630. Thus, in this patent application, 1,3-bis(trimethylsilyl)urea (BSU) is obtained in a yield of 99% after reaction for 20 minutes between hexamethyldisilazane (HMDZ) and urea, used in an HMDZ/urea molar ratio equal to 1.187 in ethyl acetate in the presence of saccharin used in a proportion of 1 mol % relative to the urea used.

Although these catalysts reduce the reaction time, they have the major drawback of remaining in the compounds (I) and consequently result in instability of the products (I) on storage, a reduction in their resistance to hydrolysis and colorations. All these drawbacks are prohibitive for certain industrial applications such as, in particular, the manufacture of antibiotics.

In addition, the removal of the said catalysts, which are generally in very small amounts in the products (I), would entail long and expensive purification operations, which would be prohibitive as regards the production efficiency of an industrial process.

In most of the processes for manufacturing the products (I) mentioned in the literature, a solvent (or a mixture of solvents) is used. Among the solvents used, mention will be made of aromatic carbides such as benzene or toluene (U.S. Pat. No. 3,992,428), alkyl acetates such as ethyl acetate (EP 43630), ethers such as di-n-butyl ether, dioxane or THF, ketones such as acetone, chlorinated hydrocarbons such as $CH_2Cl_2$ or 1,2-dichloroethane (Ts. Gueorguieva et al. Farmatsiya, 31(2) 1981 pages 1 to 5), siloxanes such as hexamethyldisiloxane mentioned in U.S. Pat. No. 3,992,428 and the disilazanes (II) which are also reagents.

Thus, Patent Application DE 4 041 651 describes a process for preparing BSU using hexamethyldisilazane (HMDZ) as reagent and solvent.

The process consists in heating, at the reflux point of the HMDZ, 10 g of urea (having a water content of 0.3% by weight), i.e. 0.151 mol. in 180 ml of HMDZ, i.e. 0.853 mol, in the presence of 1 g of cation exchanger and 0.1 g of water. After cooling, 30 g of BSU precipitates, which corresponds to a yield of 86%.

After reprocessing the filtrate, a further 4.5 g of BSU are recovered, which brings the final yield to 99%.

Although it is attractive to use HMDZ as reagent and as solvent, it is nevertheless found that this way of working has the drawback in that it is necessary to process the filtrate in order to recover an appreciable portion of BSU which has dissolved.

In addition, the said BSU recovered is liable to contain impurities and, consequently, requires a purification operation.

Given also the high price of HMDZ, its use in large amounts is prohibitive as regards the production efficiency of an industrial process.

Thus, an attempt was made to improve the process mentioned above by reducing the amounts of HMDZ, eliminating the water and the cation exchanger and using trimethylchlorosilane (TMCS) as catalyst. It was observed that such a process could only work with an HMDZ/urea molar ratio in the region of 3, since a lower ratio gave a thick reaction medium which is difficult to stir with the usual devices. Furthermore, it is difficult to remove all of the HMDZ from the BSU obtained.

During these tests, the importance was also noted of the particle size of the urea, which is virtually insoluble in HMDZ at reflux. This product is only commercially available in the form of coarse grains or beads ranging from 1 to 2 mm in diameter. The use of such course grains of urea entails a long and incomplete reaction and gives a final product which contains unconverted urea which is very difficult to remove.

In order to increase its conversion, the urea can be ground and used in the form of a fine powder. Working in this way, however, burdens the process with an expensive grinding operation, and the conversion of the urea is also not totally complete.

SUMMARY OF THE INVENTION

A process has now been found for preparing bis-silyl ureas (I), which comprises reacting in a solvent, urea and a disilazane (II) according to equation (1), said process comprising as a preferred comprehensive embodiment, conducting the following steps:

a) placing in contact, with stirring, a solvent, a disilazane and urea,
b) bringing the medium obtained in a) to a temperature equal to or less than the boiling point of the said solvent,
c) maintaining, from the start of evolution of the ammonia, a temperature equal to or different from that used in b) and preferably less than the boiling point of the solvent,
d) maintaining this temperature until virtually all of the ammonia has been evolved, optionally followed by stripping off the residual ammonia with an inert gas,
e) cooling the reaction medium, and
f) recovering the precipitated bis-silyl urea (I) by filtration, optionally washing it with a solvent identical to or different from the one used in a), and then drying it under reduced pressure;

the said process being characterized in that the solvent used in a) for the reaction and optionally in f) to wash the bis-silyl urea (I) is an aliphatic nitrile RCN in which R represents a linear or branched aliphatic hydrocarbon-based radical containing a number of carbon atoms ranging from 1 to 5 and preferably ranging from 1 to 3.

As illustrations of such aliphatic nitrites which can be used according to the present invention, mention will be made of: acetonitrile, propionitrile, butyronitrile. Acetonitrile will preferably be used.

According to the present invention, the solvent for washing the bis-silyl urea I is preferably identical to the reaction solvent used in a).

According to one particularly preferred variant of the process according to the invention, the reaction solvent used in a) can consist totally or partially of the filtrates arising from the filtration and optionally of the condensates arising from the drying of the bis-silyl urea (I) from a previous operation. In the event that the filtrates arising from the filtration and optionally the condensates arising from the drying of the bis-silyl urea (I) are partially recycled, the remainder is provided by fresh solvent.

The reaction solvent used in a) preferably all consists of filtrates arising from the filtration of a previous operation.

According to the present invention, the starting urea $(H_2N)_2C(O)$ can be in various forms such as beads or granules of different particle size.

A urea in the form of beads ranging from 1 to 2 mm in diameter will preferably be used.

According to the present invention, the urea and the disilazane (II) will be used in a disilazane (II)/urea molar ratio ranging from 1 to 1.3 and preferably ranging from 1.05 to 1.25.

The solvent will be used according to a solvent/disilazane (II) weight ratio ranging from 1 to 5 and preferably ranging from 2 to 3.

The process is generally performed at atmospheric pressure and under inert atmosphere.

The reaction progress is monitored by assaying the amount of $NH_3$ evolved as a function of the reaction time.

The bis-silyl urea (I) is isolated by filtration/centrifugation and then dried, preferably under reduced pressure.

In the event that the conversion of the urea is quantitative, the bis-silyl urea (I) can be recovered from the reaction medium after evaporating off the solvent under reduced pressure followed by drying under reduced pressure. According to the process of the present invention, the distillates, such as the filtrates, can be recycled into the next operation.

The process according to the present invention applies most particularly to the synthesis of 1,3-bis(trimethylsilyl) urea from urea and hexamethyldisilazane.

The process according to the invention has the advantage of being able to use a commercially available urea, of "technical" grade, which is in the form of beads or granules that require no grinding.

The products obtained no longer contain urea and are of sufficient purity, not requiring purification in order to be used directly in the preparation of medicinal products such as antibiotics.

According to the present invention, the filtrates and/or condensates consisting mainly of the reaction solvent and optionally of the washing solvent can be recycled several times without any reduction in the purity of the products obtained being observed.

In addition, the compounds which may be present in the filtrates and condensates consist essentially of the dissolved unconverted reagents, by product compounds such as siloxanes arising from the action of water on the disilazanes, the said water being liable to be present in a very small amount in the reagents and/or solvents, and of the bis-silyl urea (I) itself which may have been dissolved, and are not of a nature to disrupt the reaction kinetics. It has been found that the concentration of the by product compounds increases very slowly in the course of the recyclings. This is another advantage of the process, namely the ability to carry out a large number of recyclings of the solvent without it being necessary to carry out any purification of the said solvent.

However, as a function of the water content of the reagents and solvents used and in order to avoid an excessive accumulation of these side compounds, these by product compounds can be removed from the filtrates by distillation after a certain number of recyclings. The solvent thus purified can be reused.

Another advantage is that it is thus possible to use reagents and solvents without it being necessary to carry out a thorough drying.

The examples below illustrate the invention.

GENERAL CONDITIONS

Reagents and Solvents Used:

Urea: in the form of beads ranging from 1 to 3 mm in diameter;
without anticaking agent.
Purity: 97.6%.

Hexamethyldisilazane—HMDZ:
 Purity: 95.6%.
Acetonitrile:
 Purity: 99.8%.

The determination of the purity of the bis(trimethylsilyl) urea (BSU) and of the compounds present in the filtrates was carried out by gas chromatography and potentiometry in an anhydrous medium.

Brief Description of the Drawing

The attached

EXAMPLE 1

Preparation of 1,3-bis(trimethylsilyl)urea (BSU)

Figure 1:
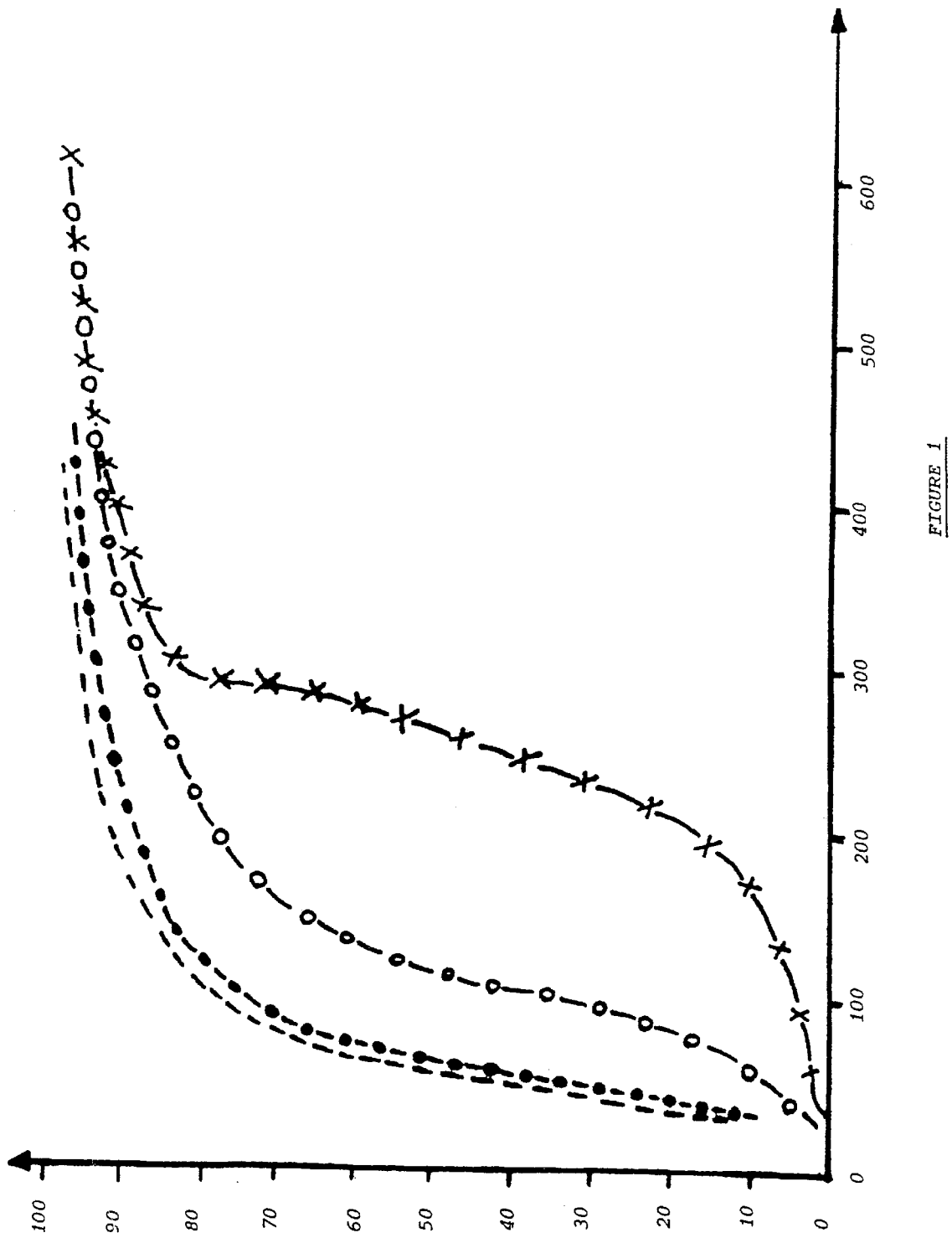
FIG. 1 is a graph wherein the percentage of $NH_3$ evolved as a function of the reaction time is represented by the curve -X-X-X.

The following reagents:
 112.5 g of urea (1.827 mol),
 337.5 g of HMDZ (1.999 mol),
 707.4 g of fresh acetonitrile,
are introduced, with stirring, into a 1.5 litre reactor equipped with a stirrer, heating means and a vent outlet connected to a scrubber column, and the mixture is then heated to the reflux point of the acetonitrile (81–82° C.). When $NH_3$ is detected in the scrubber column, the temperature is reduced to about 70° C. and maintained until all of the $NH_3$ has evolved.

The percentage of $NH_3$ evolved as a function of the reaction time is represented in FIG. 1 by the curve -X-X-X. In FIG. 1, the percentage of $NH_3$ expressed as a percentage by weight is given on the Y-axis and the reaction time expressed in minutes is given on the x-axis. The reaction medium is cooled to about 20° C. and then filtered. The cake is rinsed with 135 g of fresh acetonitrile. 359.2 g of dry BSU are obtained in a purity of 98.8%, which corresponds to 354.9 g of pure BSU, i.e. 1.736 mol.

The mass of filtrates is 758.75 g and the mass of condensates resulting from the drying is 47.1 g consisting mainly of acetonitrile.

The filtrates are analysed and contain, by weight:
 0.3% of unconverted urea, i.e. 2.35 g (0.039 mol),
 2% of HMDZ,
 1.91% of hexamethyldisiloxane (HMDO),
 0.75% of dissolved BSU, i.e. 5.69 g (0.0278 mol),
 94.55% of acetonitrile, i.e. 717.4 g.
Conversion of the Urea: 97.87%

The net molar yield of filtered and dried BSU relative to the urea used is equal to 96.2%.

EXAMPLES 2, 3 AND 4

According to the Invention with Recycling of the Filtrates

The process is performed according to operating conditions identical to those of Example 1, with amounts of reagents as indicated in Table 1.

The reaction solvent no longer consists of fresh acetonitrile, but rather consists totally of the filtrates from Example 1 for Example 2, from Example 2 for Example 3, and from Example 3 for Example 4.

The washing solvent is fresh acetonitrile.

The amounts by weight of fresh acetonitrile for the washes and the amounts by weight of filtrates are indicated in Table 1.

The following are also indicated in this table 1:
 the weight of the wet BSU crystals (in g),
 the weight of the filtrates (in g),
 the weight of the condensates (in g),
 the weight of dry BSU (in g),
 the purity of the dry BSU in %,
 the weight of pure BSU (in g) and the corresponding number of mols
 the analysis of the filtrates (main constituents),
 the conversion of the urea, denoted by $C_{urea}$,
 the net molar yield denoted by $Y_{BSU}$.

TABLE 1

|  | 2 | 3 | 4 |
|---|---|---|---|
| UREA: weight (g); mol | 112.5;1.827 | 112.5;1.827 | 108.7;1.766 |
| HMDZ: weight (g); mol | 323.1;1.914 | 324;1.919 | 324.7;1.923 |
| Filtrates: weight (g) | 721.4 | 721.15 | 724.7 |
| Fresh washing acetonitrile (g) | 130 | 101 | 70 |
| FILTRATION: |  |  |  |
| Weight of wet BSU crystals (g) | 417.2 | 419.4 | 449 |
| Weight of filtrates (g) | 772.8 | 731.7 | 683.9 |
| DRYING: |  |  |  |
| Dry BSU (g) | 371.3 | 367.1 | 370 |
| Purity of the BSU (%) | 99.1 | 99.4 | 99.9 |
| Weight of pure BSU (g); mol | 367.95;1.800 | 364.89;1.785 | 369.63;1.808 |
| Weight of the condensates (g) | 45.45 | 43.95 | 74.8 |
| ANALYSIS OF THE FILTRATES (% by weight): |  |  |  |
| UREA | 0.43 | 0.50 | 0.33 |
| HMOZ | 1.81 | 1.68 | 2.51 |
| HMDO | 4.23 | 5.11 | 5 |
| BSU | 1.04 | 0.57 | 0.34 |
| $CH_3CN$ | 91.77 | 91.4 | 90.47 |
| $C_{urea}$ (%) | 97.1 | 96.8 | 98 |
| $Y_{BSU}$ (%) | 96.6 | 95 | 99 |

The percentages of $NH_3$ evolved as a function of the reaction time are represented in FIG. 1, respectively, by:
 —o—o—o for Example 2,
 —●—●—● for Example 3, and
 --- - - - for Example 4.

In a broader aspect of this invention, there is provided in a process for preparing bis-silyl ureas by reacting urea and a disilazane in a solvent, the improvement wherein the solvent is an aliphatic nitrile, particularly acetonitrile. Also, processes intermediate in complexity between the latter process and the preferred embodiment are incorporated herein.

Still another aspect of the invention provides intermediate compositions of at least one reactant with or without product or byproducts, wherein the solvent is an aliphatic nitrile, particularly acetonitrile.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 99/07206, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for preparing bis-silyl ureas of formula (I) $R^1R^2R^3$-SiNHC(O)NHSi-$R^4R^5R^6$ (I) in which $R^1$, $R^2$, $R^3$, $R^4$, $R^5$ and $R^6$, which may be identical or different, represent a linear or branched aliphatic hydrocarbon-based radical containing a number of carbon atoms ranging from 1 to 5, a phenyl radical, a benzyl radical or a phenethyl radical, which comprises reacting, in a solvent, urea and a disilazane of formula (II): $R^1R^2R^3$-Si-NH-Si-$R^4R^5R^6$ (II) in which $R^1$, $R^2$, $R^3$, $R^4$, $R^5$ and $R^6$ have the same meanings as in formula (I), the said process comprising conducting the following steps:

a) placing in contact, with stirring, a reaction solvent, a disilazane and urea,
   b) bringing the medium obtained in a) to a sufficient temperature equal to or less than the boiling point of the said solvent so as to evolve ammonia,
   c) providing, from the start of evolution of the ammonia, a temperature equal to or different from that used in b) until virtually all of the ammonia has been evolved, optionally followed by stripping off the residual ammonia with an inert gas,
   d) cooling the reaction medium, and
   e) recovering resultant the bis-silyl urea (I), optionally washing it with a solvent identical to or different from the one used in a), and then drying it under reduced pressure;

the improvement comprising utilizing as the reaction solvent used in a) and optionally in e) to wash the bis-silyl urea (I) an aliphatic nitrile RCN in which R represents a linear or branched aliphatic hydrocarbon-based radical containing from 1 to 5 carbon atoms.

2. A process according to claim 1, wherein the aliphatic nitrile contains carbon atoms 1 to 3.

3. A process according to claim 1, wherein the aliphatic nitrile is acetonitrile, propionitrile or butyronitrile.

4. A process according to claim 1, wherein the aliphatic nitrile is acetonitrile.

5. A process according to claim 1, wherein the urea and the disilazane (II) have a disilazane (II)/urea molar ratio ranging from 1 to 1.3.

6. A process according to claim 5, where in the disilazane (II)/urea molar ratio ranges from 1.05 to 1.25.

7. A process according to claim 1, having a solvent/disilazane (II) weight ratio from 1 to 5.

8. A process according to claim 7, wherein the solvent/disilazane (II) weight ratio ranges from 2 to 3.

9. A process according to claim 1, wherein the urea is used in the form of beads.

10. A process according to claim 1, wherein the reaction solvent is comprised in a) totally or partially of the filtrates arising from the filtration and optionally of the condensates arising from the drying of bis-silyl urea (I).

11. A process according to claim 10, wherein the reaction solvent used in a) consists totally of the filtrates.

12. A process according to claim 10, wherein the reaction solvent is comprised partially of the filtrates fresh solvent and optionally of the condensates.

13. A process according to claim 1, wherein the solvent used in step e) to wash the bis-silyl urea (I) is identical to the reaction solvent used in step a).

14. A process according to claim 1, wherein the disilazane (II) is hexamethyldisilazane.

15. In a process for preparing bis-silyl ureas comprising reaction urea and a disilazane in a reaction solvent, the improvement wherein the reaction solvent is an aliphatic nitrile of the formula RCN wherein R is an aliphatic hydrocarbon having 1–5 carbon atoms.

16. A process according to claim 15, wherein the reaction solvent is acelonitrile.

17. A process according to claim 16, wherein the disilazane is hexamethyldisilazane.

18. A composition comprising an aliphatic nitrile of the formula RCN wherein R is an aliphatic hydrocarbon having 1–5 carbon atoms, and at least one member selected from the group consisting of urea and a disilazane.

19. A composition according to claim 18, comprising both urea and a disilazane.

20. A composition according to claim 18, wherein the disilazane is hexamethyldisilazane.

21. A composition comprising an aliphatic nitrile of the formula RCN wherein R is an aliphatic hydrocarbon having 1–5 carbon atoms, and a bis-silyl urea.

22. A composition according to claim 21, wherein the bis-silyl urea is bis(trimethylsilyl) urea.

* * * * *